United States Patent
Shirakawa

(10) Patent No.: US 10,054,585 B2
(45) Date of Patent: Aug. 21, 2018

(54) DIAGNOSIS OF RESPIRATORY TRACT INFECTIOUS DISEASE USING URINE SPECIMENS

(71) Applicant: Mochida Pharmaceutical Co., Ltd., Tokyo (JP)

(72) Inventor: Kamon Shirakawa, Tokyo (JP)

(73) Assignee: Mochida Pharmaceutical Co., Ltd., Tokyo (JP)

(*) Notice: Subject to any disclaimer, the term of this patent is extended or adjusted under 35 U.S.C. 154(b) by 0 days.

(21) Appl. No.: 15/047,983

(22) Filed: Feb. 19, 2016

(65) Prior Publication Data

US 2016/0169889 A1 Jun. 16, 2016

Related U.S. Application Data

(63) Continuation of application No. 14/118,302, filed as application No. PCT/JP2012/062797 on May 18, 2012, now Pat. No. 9,297,802.

(30) Foreign Application Priority Data

May 19, 2011 (JP) ................................ 2011-112699

(51) Int. Cl.
| | | |
|---|---|---|
| *G01N 33/68* | (2006.01) | |
| *A61K 45/00* | (2006.01) | |
| *A61P 11/00* | (2006.01) | |
| *A61P 31/04* | (2006.01) | |
| *G01N 33/569* | (2006.01) | |
| *A61K 31/407* | (2006.01) | |
| *A61K 31/43* | (2006.01) | |
| *A61K 31/665* | (2006.01) | |
| *A61K 38/16* | (2006.01) | |
| *A61K 31/65* | (2006.01) | |
| *A61K 31/7008* | (2006.01) | |
| *A61K 31/7028* | (2006.01) | |
| *A61K 38/02* | (2006.01) | |

(52) U.S. Cl.
CPC ...... *G01N 33/56911* (2013.01); *A61K 31/407* (2013.01); *A61K 31/43* (2013.01); *A61K 31/65* (2013.01); *A61K 31/665* (2013.01); *A61K 31/7008* (2013.01); *A61K 31/7028* (2013.01); *A61K 38/02* (2013.01); *A61K 38/16* (2013.01); *A61K 45/00* (2013.01); *G01N 2333/70596* (2013.01); *G01N 2800/12* (2013.01); *G01N 2800/52* (2013.01)

(58) Field of Classification Search
None
See application file for complete search history.

(56) References Cited

U.S. PATENT DOCUMENTS

| 2006/0068445 A1 | 3/2006 | Furusako et al. |
|---|---|---|
| 2011/0086381 A1 | 4/2011 | Naito |
| 2014/0213507 A1 | 7/2014 | Shirakawa |

FOREIGN PATENT DOCUMENTS

| CN | 1711283 A | 12/2005 |
|---|---|---|
| EA | 005776 B1 | 6/2005 |
| EP | 1571160 A1 | 9/2005 |
| EP | 1 746 104 A1 | 1/2007 |
| WO | WO 02/095411 A1 | 11/2002 |
| WO | WO 2005/018535 A2 | 3/2005 |
| WO | WO 2005/108429 A1 | 11/2005 |
| WO | WO 2008/104321 A1 | 9/2008 |
| WO | WO 2009/142303 A1 | 11/2009 |

OTHER PUBLICATIONS

Shozushima et al., "Usefulness of presepsin (sCD14-ST) measurements as a marker for the diagnosis and severity of sepsis that satisfied diagnostic criteria of systemic inflammatory response syndrome," J. Infect Chemother., Dec. 2011 (published online May 12, 2011), 17(6):764-769.
U.S. Appl. No. 14/118,304, filed May 18, 2012, Kamon Shitakawa.
American Lung Association, "Acute respiratory distress syndrome (ARDS)," American Lung Association Lung Disease Data, 2008, 9-12.
Ball et al., "Antibiotic therapy of community respiratory tract infections: strategies for optimal outcomes and minimized resistance emergence," Journal of Antimicrobial Chemotherapy, 2002, 49:31-40.
Christ-Crain et al., "Effect of procalcitonin-guided treatment on antibiotic use and outcome in lower respiratory tract infections: cluster-randomised, single-blinded intervention trial," The Lancet, Feb. 21, 2004, 363:600-607.
Christ-Crain et al., "Procalcitonin Guidance of Antibiotic Therapy in Community-acquired Pneumonia, A Randomized Trial," Am. J. Respir. Crit. Care Med., 2006, 174:84-93.
Endo et al., "Usefulness of presepsin in the diagnosis of sepsis in a multicenter prospective study," J. Infect. Chemother., Jun. 2012, 18:891-897.
Liu et al., "Role of Presepsin (sCD14-ST) and the CURB65 scoring system in predicting severity and outcome of community-acquired pneumonia in an emergency department," Respir. Med., 2014, 108:1204-1213.
Livermore, "The need for new antibiotics," Clin. Microbiol. Infect., 2004, 10(Suppl. 4):1-9.
Marcos et al., "Expression, regulation and clinical significance of soluble and membrane CD14 receptors in pediatric inflammatory lung diseases," Respiratory Research, 2010, 11:32(1-13).
Martin et al., "Relationship between soluble CD14, lipopolysaccharide binding protein, and the alveolar inflammatory response in (Continued)

*Primary Examiner* — Julie Ha
*Assistant Examiner* — Kristina M Hellman
(74) *Attorney, Agent, or Firm* — Foley & Lardner LLP

(57) ABSTRACT

Methods for detecting respiratory infection associated with bacterial infection are described, in which the values of soluble CD14 antigen subtype ("sCD14-ST") in the urine sample can be used to select a patient with a respiratory infection to whom antibiotic can be beneficially administered. The methods of this disclosure can also be used to determine the timing for ending administration of the antibiotic to the patient with respiratory infection associated with bacterial infection.

20 Claims, 4 Drawing Sheets

(56) References Cited

OTHER PUBLICATIONS patients with acute respiratory distress symdrome," Am. J. Respir. Crit. Care. Med., 1997, 155:937-944.
Ozcengiz et al., "Recent advances in the biosynthesis of penicillins, cephalosporins and clavams and its regulation," Biotechnol. Adv., 2013, 31:287-311.
The Japanese Respiratory Society Guidelines for the Management of Adult Community-Acquired Pneumonia, Asu no Rinsho, Pocket Edition, Jun. 25, 2007, 19(1):41-61, with partial English translation of indicated portion of p. 48.
Yaegashi et al,. "Evaluation of a newly identified soluble CD14 subtype as a marker for sepsis," J. Infect. Chemother., 2005, 11:234-238.
Bussolati et al., "Urinary soluble CD14 mediates human proximal tubular epithelial cell injury induced by LPS," International Journal of Molecular Medicine, Oct. 2002, 10(4):441-449.
Jackson et al., "Soluble urinary CD14 after intravesical bacille Calmette-Guérin immunotherapy for carcinoma in situ," British Journal of Urology, Nov. 1997, 80(5):766-771.
Sundan et al., "Soluble CD14 from urine copurifies with a potent inducer of cytokines," Eur. J. Immunol., Aug. 1994, 24(8):1779-1784.
Canadian Patent Office office action, Appl. No. 2,836,565, dated Feb. 27, 2018.
Decision to Grant, Russian Appl. 2013156365, Nov. 27, 2017, 21 pages.

Number of days elapsed after diagnosis of pneumonia

DIAGNOSIS OF RESPIRATORY TRACT INFECTIOUS DISEASE USING URINE SPECIMENS

CROSS-REFERENCE TO RELATED APPLICATIONS

This application is a Continuation of U.S. application Ser. No. 14/118,302, which is the U.S. National Stage application of PCT/JP2012/062797, filed May 18, 2012, which claims priority from Japanese application JP 2011-112699, filed May 19, 2011.

The instant application contains a Sequence Listing which has been submitted in ASCII format via EFS-WEB and is hereby incorporated by reference in its entirety. Said ASCII copy, created on Jan. 31, 2016, is named sequence.txt and is 4 KB.

TECHNICAL FIELD

The present invention relates to a method for detecting respiratory infection associated with bacterial infection, a method for selecting patients with respiratory infection to receive an antibiotic, and a method for determining the timing for ending administration of an antibiotic to a patient with respiratory infection receiving the antibiotic. In addition, the present invention also relates to a method for treating respiratory infection associated with bacterial infection.

BACKGROUND ART

Respiratory infection is a disease frequently encountered in clinical sites. There are two types of respiratory infection, namely, respiratory infection caused by viral infection and respiratory infection caused by bacterial infection. Antibiotics have no effects on viral respiratory infection. In principle, upon administration of antibiotics, a causative microorganism is first identified, and an antibiotic used therefor is then selected depending on the sensitivity of the causative microorganism to drugs, etc. However, since it takes a long period of time to search for such a causative microorganism by blood culture or examination of sputum, in reality, a treatment using antibiotics has been started before determination of a pathogen in almost all cases. Moreover, since the detection sensitivity of bacteria is not necessarily high in such blood culture or examination of sputum, even if the results are negative, bacterial infection cannot be denied. Thus, antibiotics are used even for patients with respiratory infection suspected to have bacterial infection. Hence, administration of antibiotics to patients who do not need them causes an increase in resistant bacteria (Non Patent Literature 1).

For the proper use of antibiotics, it is necessary that the presence or absence of bacterial infection in respiratory infection can be promptly and precisely diagnosed in clinical sites. As such a diagnostic marker, the usefulness of procalcitonin has been studied. It has been reported that when lower respiratory tract infection or pneumonia is treated with antibiotics, while using the concentration of procalcitonin in blood as an indication, the amounts of the antibiotics used can be decreased (Non Patent Literature 2 and Non Patent Literature 3).

Procalcitonin has also been used as a diagnostic marker for sepsis. In this case, procalcitonin is used as an indication, such that when the procalcitonin concentration in blood is 0.5 ng/mL or higher, the subject is determined to have sepsis, and when the procalcitonin concentration is 2.0 ng/mL or higher, the subject is determined to have severe sepsis. On the other hand, when procalcitonin is used as a marker for lower respiratory tract infection or pneumonia, a change in a blood procalcitonin concentration that ranges from 0.1 to 0.5 ng/mL must be detected, and thus, there is a restriction that a highly sensitive assay must be used. Moreover, it has also been reported that, since procalcitonin is stably present in blood, the blood procalcitonin concentration is relatively slowly lowered even in a case in which the treatment has been successful (Patent Literature 1). It is considered that when the half-life of procalcitonin in blood is long, a concentration change is hardly detected.

As a novel marker for sepsis that is superior to procalcitonin, the usefulness of sCD14-ST (soluble CD14 antigen subtype; alias name: presepsin) has been studied. It has been reported that even if such sCD14-ST is used in a comparison between a patient with sepsis and a patient with systemic inflammatory response syndrome (SIRS) that is difficult to be distinguished from sepsis, it shows a high value in the blood of the sepsis patient. Thus, it has been considered that sCD14-ST is useful as a diagnostic marker for sepsis (Non Patent Literature 4 and Patent Literature 2).

Furthermore, it has also been reported that sCD14-ST is generated in a process in which cells englobe and digest foreign microorganisms or foreign matters, and that an increase in the concentration of sCD14-ST in synovial fluid can be detected in a disease that involves phagocytosis attended with autoimmune response or infection in local sites, such as arthritis (Patent Literature 3).

CITATION LIST

Patent Literature

Patent Literature 1: International Publication WO2008/104321
Patent Literature 2: International Publication WO2005/108429
Patent Literature 3: International Publication WO2009/142303

Non Patent Literature

Non Patent Literature 1: Ball et al., Journal of Antimicrobial Chemotherapy 49: 31-40, 2002.
Non Patent Literature 2: Christ-Crain et al., The Lancet 363: 600-607, 2004.
Non Patent Literature 3: Christ-Crain et al., Am J Respire Crit Care Med 174: 84-93, 2006.
Non Patent Literature 4: Yaegashi et al., Journal of Infection and Chemotherapy 11: 234-238, 2005.

SUMMARY OF INVENTION

Technical Problem

It is an object of the present invention to provide a method for appropriately selecting patients with respiratory infection to whom an antibiotic is to be administered, and a method for adjusting the administration period of an antibiotic. That is to say, the present invention is directed towards achieving the object that is the proper use of antibiotics for respiratory infection. Specifically, the present invention provides a method for detecting respiratory infection associated with bacterial infection, a method for selecting patients with respiratory infection to receive an antibiotic, and a method for determining the timing for ending administration of an antibiotic to a patient with respiratory infection receiving the antibiotic. To achieve these objects, it has been desired to develop a novel marker used to appropriately select respiratory infection associated with bacterial infection. In addition, it has also been desired to develop a sensitive marker, the concentration of which promptly decreases with diminution and/or disappearance of bacterial infection in respiratory organs. Moreover, the present invention provides a method for treating respiratory infection associated with bacterial infection.

Solution to Problem

The present inventor has found that it becomes possible to appropriately select patients with respiratory infection to whom an antibiotic is to be administered, and also to adjust the administration period of an antibiotic, by using a measured value of sCD14-ST in urine as an indication, thereby completing the present invention.

More specifically, the present invention includes the following features.

The present invention provides the following methods for detecting respiratory infection associated with bacterial infection:

(1-1) A method for detecting respiratory infection associated with bacterial infection, comprising measuring sCD14-ST in a urine sample derived from a subject.
(1-2) A method for detecting respiratory infection associated with bacterial infection, which comprises the following steps of:
1) measuring sCD14-ST in a urine sample derived from a subject; and
2) determining whether or not the subject is affected with respiratory infection associated with bacterial infection by using a measured value of sCD14-ST in the sample as an indication.
(1-3) A method for detecting respiratory infection associated with bacterial infection, which comprises the following steps of:
1) measuring sCD14-ST in a urine sample derived from a subject;
2) comparing a measured value of sCD14-ST in the sample with a normal value; and
3) determining whether the measured value of the sample is higher than the normal value.
(1-4) The method according to above (1-3), wherein, as the normal value, an average value of measured values of sCD14-ST in urine samples of normal subjects+2SD is used.
(1-5) A method for detecting respiratory infection associated with bacterial infection, comprising the step of:
1) measuring sCD14-ST in a urine sample derived from a subject.
(1-6) The method for detecting according to above (1-5), which further comprises the following step of:
2) comparing the measured value of sCD14-ST in the urine sample with a normal value.
(1-7) The method for detecting according to above (1-6), which further comprises the following step of:
3) determining whether the measured value is higher than the normal value or not.
(1-8) The method according to any of above (1-1) to (1-7), wherein the respiratory infection associated with bacterial infection is lower respiratory tract infection or pneumonia.
(1-9) The method according to any of above (1-1) to (1-8), wherein a differential diagnosis of respiratory infection caused by viral infection is possible.

(1-10) The method according to any of above (1-1) to (1-9), wherein, in addition to measurement of sCD14-ST in a urine sample derived from a subject, at least one kind of causative microorganism test is performed.
(1-11) The method according to above (1-10), wherein the causative microorganism test is at least one selected from the group consisting of stained smear test, antigen test of influenza virus, adenovirus, legionella, chlamydia, mycoplasma, aspergillus, candida, cryptococcus, cytomegalovirus, or pneumococcus, and culture test of blood, sputum or bronchoalveolar lavage fluid.
(1-12) A marker for respiratory infection associated with bacterial infection, comprising sCD14-ST.
(1-13) The marker according to above (1-12), further comprising at least one selected from the group consisting of inflammation markers including TNF-α, lactate dehydrogenase, sialic acid, IL-1β, IL-6, and IL-10, markers associated with thrombus and hemostasis including activated partial thromboplastin time, platelet count, fibrinogen, items of the diagnostic criteria for DIC, protein C, D-dimer, thrombin-antithrombin III complex, and prothrombin fragment F1+2, infection markers including procalcitonin (PCT), C-reactive protein (CRP), blood urea nitrogen, white blood cell count, endotoxin, adrenomedullin, proadrenomedullin, MR-proADM, B-type natriuretic peptide, trigger receptors expressed on myeloid cell-1, and HMGB1, stress markers including cortisone and copeptin, and markers for interstitial pneumonia including KL-6, SP-A, SP-D, and MCP-1.
(1-14) A method for detecting respiratory infection associated with bacterial infection, wherein sCD14-ST in a urine sample derived from a subject and at least one biomarker other than sCD14-ST are measured.
(1-15) The method according to above (1-14), wherein the biomarker other than sCD14-ST is at least one marker stated in above (1-13).

The present invention provides the following methods for selecting patients with respiratory infection to receive an antibiotic:

(2-1) A method for selecting patients with respiratory infection to receive an antibiotic, comprising: measuring sCD14-ST in urine samples derived from patients.
(2-2) A method for selecting patients with respiratory infection to receive an antibiotic, which comprises the following steps of:
1) measuring sCD14-ST in urine samples derived from patients; and
2) determining whether or not patients are affected with respiratory infection associated with bacterial infection by using measured values of sCD14-ST in the samples as an indication.
(2-3) A method for selecting patients with respiratory infection to receive an antibiotic, which comprises the following steps of:
1) measuring sCD14-ST in urine samples derived from patients;
2) comparing measured values of sCD14-ST in the samples with a normal value; and
3) determining whether the measured values of the samples are higher than the normal value.
(2-4) The method according to above (2-3), wherein, as the normal value, an average value of measured values of sCD14-ST in urine samples of normal subjects+2SD is used.
(2-5) The method according to any of above (2-1) to (2-4), wherein the respiratory infection is lower respiratory tract infection or pneumonia.

The present invention provides the following methods for determining the timing for ending administration of an antibiotic to a patient with respiratory infection receiving the antibiotic.

(3-1) A method for determining the timing for ending administration of an antibiotic to a patient with respiratory infection receiving the antibiotic, wherein a measured value of sCD14-ST in a urine sample derived from the patient is used as an indication.

(3-2) A method for determining the timing for ending administration of an antibiotic to a patient with respiratory infection receiving the antibiotic, which comprises the following steps of:

1) measuring sCD14-ST in a urine sample derived from a patient;

2) comparing the measured value of sCD14-ST in the sample with a predetermined reference value; and 3) when the measured value of the sample is lower than the predetermined reference value, determining to end administration of the antibiotic.

(3-3) The method according to above (3-2), wherein, as the predetermined reference value, an average value of measured values of sCD14-ST in urine samples of normal subjects+SD is used.

(3-4) A method for selecting patients to end administration of an antibiotic from patients with respiratory infection receiving the antibiotic by using measured values of sCD14-ST in urine samples derived from patients as indications.

(3-5) A method for selecting patients to end administration of an antibiotic from patients with respiratory infection receiving the antibiotic, which comprises the following steps of:

1) measuring sCD14-ST in urine samples derived from patients;

2) comparing measured values of sCD14-ST in samples with a predetermined reference value; and 3) when the measured values of the samples are lower than the predetermined reference value, determining to end administration of the antibiotic.

(3-6) The method according to above (3-5), wherein, as the predetermined reference value, an average value of measured values of sCD14-ST in urine samples of normal subjects+SD is used.

(3-7) The method according to any of above (3-1) to (3-6), wherein the respiratory infection is lower respiratory tract infection or pneumonia.

The present invention provides the following treating methods of respiratory infection associated with bacterial infection.

(4-1) A method for treating respiratory infection associated with bacterial infection, which comprises the following steps of:

1) measuring sCD14-ST in urine samples derived from patients;

2) selecting patients to receive an antibiotic by using measured values of sCD14-ST in the samples as an indication; and 3) administering the antibiotic to the selected patients.

(4-2) The method according to above (4-1), wherein the step of selecting patients to receive an antibiotic by using measured values of sCD14-ST in the samples as an indication comprises the following steps of:

1) comparing measured values of sCD14-ST in the samples with a normal value; and 2) selecting patients to receive an antibiotic whose measured values in samples are higher than the normal value.

(4-3) The method according to above (4-2), wherein, as the normal value, an average value of measured values of sCD14-ST in urine samples of normal subjects+2SD is used.

(4-4) The method according to any of above (4-1) to (4-3), which further comprises the following steps of:

1) measuring over time sCD14-ST in urine samples derived from patients receiving an antibiotic;

2) comparing measured values of sCD14-ST in samples with a predetermined reference value; and 3) when the measured values of the samples are lower than the predetermined reference value, determining to end administration of the antibiotic.

(4-5) The method according to above (4-4), wherein, as the predetermined reference value, an average value of measured values of sCD14-ST in urine samples of normal subjects+SD is used.

(4-6) The method according to any of above (4-1) to (4-5), wherein the respiratory infection associated with bacterial infection is lower respiratory tract infection or pneumonia.

The present invention provides the following compositions for treating respiratory infection associated with bacterial infection.

(5-1) A composition for treating respiratory infection associated with bacterial infection, comprising an antibiotic as an active ingredient, wherein the composition is used so that sCD14-ST in a urine sample derived from a patient with suspected respiratory infection associated with bacterial infection is measured, the measured value is compared with a normal value, and when the measured value in the sample is higher than the normal value, the composition is administered to the patient.

(5-2) The composition for treating respiratory infection associated with bacterial infection according to above (5-1), wherein, as the normal value, an average value of measured values of sCD14-ST in urine samples of normal subjects+2SD is used.

(5-3) A composition for treating respiratory infection associated with bacterial infection, comprising an antibiotic as an active ingredient, wherein the composition is used so that sCD14-ST in a urine sample derived from a patient with suspected respiratory infection associated with bacterial infection is measured, the measured value is compared with a normal value, and when the measured value in the sample is higher than the normal value, the composition is administered to the patient, and sCD14-ST in urine samples during an administration period is measured over time, and when a measured value is lower than a predetermined value, administration of the composition is ended.

(5-4) The composition for treating respiratory infection associated with bacterial infection according to above (5-3), wherein, as the normal value, an average value of measured values of sCD14-ST in urine samples of normal subjects+2SD, and as the predetermined reference value, an average value of measured values of sCD14-ST in urine samples of normal subjects+SD are used.

(5-5) The composition for treating respiratory infection associated with bacterial infection according to any of above (5-1) to (5-4), wherein the respiratory infection associated with bacterial infection is lower respiratory tract infection or pneumonia.

(6) The method, marker, or composition according to any of above (1-1) to (5-5), wherein, in measurement of sCD-14 in the urine sample, an average value of measured values of patients with pneumonia associated with bacterial infection is higher than that of normal subjects, and an average value of measured values of patients with viral pneumonia is lower than that of normal subjects.

(7) The method, marker, or composition according to any of above (1-1) to (6), wherein, with regard to the measurement of sCD-14 in the urine sample, the concentration of sCD-14 in a blood sample derived from the same subject is measured, and the two measured values are then compared with each other.

Effects of Invention

According to the present invention, by using a measured value of sCD14-ST in urine as an indication, it becomes possible to appropriately select patients with respiratory infection to whom an antibiotic is to be administered, and also to adjust the administration period of the antibiotic. Antibiotics should be administered to diseases attended with bacterial infection. By measuring the concentration of sCD14-ST in urine, patients having respiratory infection associated with bacterial infection can be detected with high specificity and/or high sensitivity. Moreover, by determining the timing for ending administration of an antibiotic using a measured value of sCD14-ST in urine as an indication, the administration period of the antibiotic can be reduced. The proper use of an antibiotic for respiratory infection using a measured value of sCD14-ST in urine as an indication is useful in that it enables suppression of the emergence of multi-drug-resistant bacteria, a reduction in the treatment period, a reduction in the amount of the antibiotic used, and a reduction in medical costs, without impairing the safety and usefulness thereof.

DESCRIPTION OF EMBODIMENTS

Figure 1:
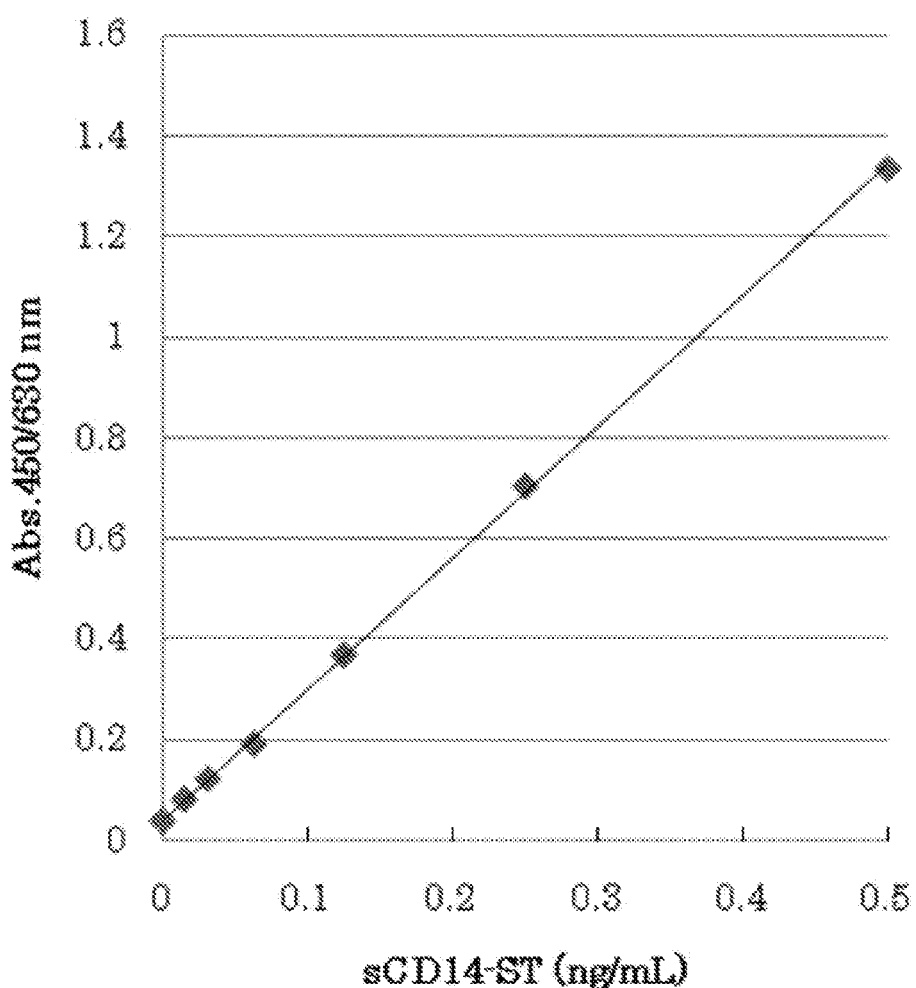
FIG. 1 is a view illustrating a standard curve of the sCD14-ST measurement system produced in Example 1.

Hereinafter, the present invention will be described in detail.

1. sCD14-ST sCD14-ST (alias name: presepsin) is a molecular species of soluble CD14. sCD14-ST is characterized in that the molecular weight measured by SDS-PAGE under non-reducing conditions is 13±2 kDa, and it retains an N-terminal portion of CD14. In addition, when such sCD14-ST is compared with the entire-length CD14, it has an amino acid sequence comprising a significant deletion on the C-terminal side thereof, and the two above proteins are different from each other in terms of conformation. Thus, they exhibit different immunogenicity. As such, the two proteins can be distinguished from each other based on antibodies to which they bind. sCD14-ST has a property that it specifically binds to an antibody produced using a peptide consisting of the 16 amino acid residues shown in SEQ ID NO: 2 as an antigen. Moreover, sCD14-ST can have any given one or more characteristics selected from that it specifically binds to a peptide consisting of the amino acids at positions 17 to 26 of the amino acid sequence shown in SEQ ID NO: 3, that it does not bind to a 3C10 antibody, that it does not bind to an MEM-18 antibody, that it does not have LPS-binding ability, and that it can be obtained from human blood. Also, sCD14-ST is characterized in that it has the amino acid sequence shown in SEQ ID NO: 1 as an N-terminal sequence thereof. More specifically, sCD14-ST can be specified by the characteristics that the N-terminus of sCD14-ST is the amino acid at position 1 of the amino acid sequence shown in SEQ ID NO: 3, and that the C-terminus thereof is any one of the amino acids at positions 59 to 90 of the amino acid sequence shown in SEQ ID NO: 3. Such sCD14-ST is disclosed in detail in International Publication WO2005/108429. The term "sCD14-ST" is used in the present specification to mean human sCD14-ST, unless otherwise specified.

For the measurement of sCD14-ST in a urine sample, an immune measurement system for specifically detecting sCD14-S, which is disclosed in International Publication WO2004/044005 or International Publication WO2005/108429, can be used, for example. Specifically, a sandwich immunoassay system comprising a combination of an antibody produced using a peptide consisting of the 16 amino acid residues shown in SEQ ID NO: 2 as an antigen with an antibody binding to a peptide consisting of the amino acids at positions 17 to 26 of the amino acid sequence shown in SEQ ID NO: 3 or with an antibody competitive to the aforementioned antibody (an F1106-13-3 antibody or an F1031-8-3 antibody) can be used.

The measured value of sCD14-ST in a urine sample can be generally indicated as a sCD14-ST concentration in urine. Upon calculation of the sCD14-ST concentration in urine, the measured value of sCD14-ST may be corrected based on the concentration of the urine according to the creatinine correction or the like. Moreover, the measured value of sCD14-ST may be any one of a quantitative value, a semiquantitative value, and a qualitative value. When such a semiquantitative value is used, the sCD14-ST concentration can be indicated as a stage of 0, 1, 2 and 3, or of +, ++ and +++. Since this stage correlates to the quantitative sCD14-ST concentration, whether or not the obtained sCD14-ST concentration is higher than the predetermined reference value may be determined based on the correlation of the semiquantitative stage with the quantitative sCD14-ST concentration. Otherwise, in the case of a semiquantitative assay, the value lower than the reference value may be set at a stage of 0 or − (minus). When a quantitative value is used, the value lower than the reference value may be set at negative, and the value higher than the reference value may be set at positive.

Urine sCD14-ST means blood sCD14-ST that has been eliminated into urine. Blood sCD14-ST is relatively promptly eliminated into urine after it has been generated. Moreover, since sCD14-ST contained in circulating blood is concentrated and is then eliminated in urine, the sCD14-ST concentration in urine is higher than the sCD14-ST concentration in blood. Accordingly, by using the measured value of sCD14-ST in a urine sample as an indication, the presence or absence of bacterial infection in respiratory organs can be sensitively detected.

2. Method for Detecting Respiratory Infection Associated with Bacterial Infection The present invention provides a method for detecting respiratory infection associated with bacterial infection, which comprises measuring sCD14-ST in a urine sample derived from a subject.

Preferred examples of the respiratory infection associated with bacterial infection include lower respiratory tract infection and pneumonia.

The lower respiratory tract infection includes acute lower respiratory tract infection and chronic lower respiratory tract infection. The acute lower respiratory tract infection includes acute tracheitis, acute bronchitis, and acute bronchiolitis. A majority of these diseases develop as a result of expansion of the viral infection of the upper respiratory tract to the lower respiratory tract. In some of these diseases, secondary infection by bacteria then takes place. When the symptoms of such secondary infection by bacteria are found, administration of antibiotics is applied. The chronic lower respiratory tract infection is a pathologic condition in which persistent bacterial infection has been found in the lower respiratory tract having organic disorders caused by bronchiectasis or chronic obstructive pulmonary disease, and it includes persistent infection and acute exacerbation. Diseases causing organic disorders to the lower respiratory tract include bronchiectasis, chronic obstructive pulmonary disease, chronic bronchitis, diffuse panbronchiolitis, obsolete pulmonary tuberculosis, pneumoconiosis, nontuberculous mycobacterial infection, allergic bronchopulmonary aspergillosis, lung fibrosis, and chronic bronchial asthma. In both cases of persistent infection and acute exacerbation, administration of antibiotics is applied.

Pneumonia includes community-acquired pneumonia and hospital-acquired pneumonia. In the present invention, community-acquired pneumonia is preferable.

The type of a subject is not particularly limited herein. A preferred subject is a person suspected to have respiratory infection based on clinical findings. Such clinical findings include at least dyspnea or coughing. In addition, preferred clinical findings include at least one selected from the group consisting of expectoration, chest pain, wheezing, shadow in chest X-ray examination, fever, and white blood cell count.

The method for detecting respiratory infection associated with bacterial infection of the present invention is characterized in that it comprises the following steps of: 1) measuring sCD14-ST in a urine sample derived from a subject; and 2) determining whether or not the subject is affected with respiratory infection associated with bacterial infection by using a measured value of sCD14-ST in the sample as an indication. More specifically, the aforementioned step 2) may comprise the following steps of: 3) comparing a measured value of sCD14-ST in the sample with a normal value; and 4) determining whether the measured value of the sample is higher than the normal value.

By comparing a measured value of sCD14-ST in the sample with the predetermined reference value, whether or not the subject has respiratory infection associated with bacterial infection can be determined. The reference value used in the method for detecting respiratory infection associated with bacterial infection of the present invention is preferably a normal value that has been set based on the measured value of sCD14-ST in a urine sample derived from a healthy subject. As such a normal value, an average value of the measurement results of sCD14-ST in the urine samples of healthy subjects, or a value standardized by defining the scope, etc., can be used. When the measured value of a sample derived from a healthy subject is almost the same as the value of the background in a measurement system, an average value of the background values in the measurement system, or a value standardized by defining the scope, etc., may be used. The background value in the measurement system means a measured value obtained in a case in which not a sample but a buffer, an assay solution or the like has been added to the measurement system. As a value obtained by standardization of the measured values of samples derived from subjects, an average value+0.5SD to +5SD (SD: standard deviation) of the measured values of healthy subjects, 5 to 95, 10 to 90, 15 to 85, or 25 to 75 percentile of the measured values of healthy subjects, or the like can be used. A preferred value is an average value+SD, +2SD or +3SD of the measured values of healthy subjects.

Upon setting a normal value based on the measured values of sCD14-ST in urine samples from healthy subjects, the value of sCD14-ST in a urine sample derived from a patient having respiratory infection associated with bacterial infection, which has previously been measured, may be used as a reference. In this case, a cutoff value that optimizes the sensitivity and/or specificity in detection of a disease can be used as a normal value. It is, for example, 5000 pg/mL.

When the measured value of a sample derived from a subject is compared with a normal value, and the measured value of the sample is higher than the normal value, it can be determined that the subject is highly likely to be affected with respiratory infection associated with bacterial infection, namely, the subject is positive. Moreover, as the measured value increases, it can be determined that the grade of the disease and/or the severity of the disease are/is high.

Since sCD14-ST is hardly generated in blood in the case of viral respiratory infection without bacterial infection, the sCD14-ST concentration in urine does not increase, either. Thus, by measuring sCD14-ST in a urine sample, respiratory infection associated with bacterial infection can be distinguished from viral respiratory infection.

Furthermore, in the method for detecting respiratory infection associated with bacterial infection of the present invention, at least one causative microorganism test may be carried out, in addition to the measurement of sCD14-ST in a urine sample derived from a subject. As such a causative microorganism test, a method may be appropriately selected from known methods such as a stained smear test, an antigen test and a culture test, and may be then used.

Further, in the method for detecting respiratory infection associated with bacterial infection of the present invention, at least one biomarker other than sCD14-ST may be measured, in addition to the measurement of sCD14-ST in a urine sample derived from a subject. As such a biomarker other than sCD14-ST, a suitable marker may be selected from among an inflammatory marker, a thrombosis/hemostasis-related marker, an infection marker, an interstitial pneumonia marker and the like, and it may be then used. Preferred examples of such a biomarker include, but are not limited to, procalcitonin, a C-reactive protein (CRP) and KL-6.

The method for detecting respiratory infection associated with bacterial infection of the present invention can also be referred to as a method for selecting patients with respiratory infection to receive an antibiotic. A subject in whom respiratory infection associated with bacterial infection has been detected is a patient who is highly likely to be affected with the respiratory infection associated with bacterial infection, and thus, the subject can be a preferred target for administration of antibiotics. Among such patients suspected to have respiratory infection based on clinical findings, patients to whom antibiotics are to be administered are those having respiratory infection associated with bacterial infection. By using a measured value of sCD14-ST in a urine sample as an indication, the presence or absence of respiratory infection associated with bacterial infection can be detected, and thus, it has become possible to select patients with respiratory infection to whom antibiotics are to be administered. That is to say, the present invention provides a method for selecting patients with respiratory infection to receive an antibiotic, which is characterized in that it comprises measuring sCD14-ST in a urine sample derived from a patient. To the method for selecting patients with respiratory infection to receive an antibiotic of the present invention, the aspect of the method for detecting respiratory infection associated with bacterial infection can directly be applied.

3. Method for Determining the Timing for Ending Administration of an Antibiotic to a Patient with Respiratory Infection Receiving the Antibiotic The present invention provides a method for determining the timing for ending administration of an antibiotic to a patient with respiratory infection receiving the antibiotic, wherein a measured value of sCD14-ST in a urine sample derived from the patient is used as an indication.

The type of a patient, to whom the method for determining the timing for ending administration of an antibiotic of the present invention is applied, is not particularly limited, as long as he/she is a patient with respiratory infection to whom an antibiotic has been administered. A preferred example is a subject, in whom Respiratory Infection Associated with Bacterial Infection has been Detected by the method described in 2. above, and who has been selected as a patient with respiratory injection to whom an antibiotic is administered.

The method for determining the timing for ending administration of an antibiotic of the present invention is characterized in that it comprises the following steps of: 1) measuring sCD14-ST in a urine sample derived from a patient; and 2) determining the timing for ending administration of an antibiotic to the patient by using a measured value of sCD14-ST in the sample derived as an indication. More specifically, the aforementioned step 2) may comprise the following steps of: 3) comparing the measured value of sCD14-ST in the sample with a predetermined reference value; and 4) when the measured value of the sample is lower than the predetermined reference value, determining to end administration of the antibiotic.

In the method for determining the timing for ending administration of an antibiotic of the present invention, when sCD14-ST in a urine sample derived from a patient is measured, it may be measured over time. In general, in the case of respiratory infection associated with bacterial infection, antibiotics are administered over a period of approximately 5 to 14 days. In order to reduce a burden on a patient and prevent the emergence of resistant bacteria, it is desired to terminate administration of an antibiotic as soon as the healing or improvement of infection can be confirmed. By measuring sCD14-ST over time, the timing for ending administration of an antibiotic can be more accurately determined. Since the sCD14-ST concentration in urine promptly decreases with diminution and/or disappearance of bacterial infection in respiratory organs, it is useful as an indication for determining termination of the treatment. The measurement period may be appropriately set. It may be set, for example, at every day, every two days, or on the day $3^{rd}$ day, $5^{th}$ day or $7^{th}$ day after initiation of the administration of an antibiotic.

Since a measured value of sCD14-ST in the sample is used as an indication for the presence or absence of bacterial infection in the patient, when the measured value of the sample is lower than the predetermined reference value, it can be determined that the infection has been healed or improved, thereby determining to end administration of the antibiotic. The reference value used in the method for determining the timing for ending administration of an antibiotic of the present invention is not particularly limited, as long as it can be used to confirm that the antibiotic has been effective. For instance, a value that is ½, ⅕ or ¹⁄₁₀ of the sCD14-ST value measured over a period from before administration of the antibiotic to 24 hours after initiation of the administration of the antibiotic can be used as a reference value. Otherwise, a normal value set based on the measured value of sCD14-ST in a urine sample derived from a healthy subject, as described in the aspect of 2. above, can also be used as a reference value. For example, it is an average value+SD, +2SD, or +3SD of healthy subjects. If the measured value of sCD14-ST is in the range of normal values, it can be considered that the infection has been healed or improved to a level equivalent to healthy subjects. Preferably, using the previously measured values of sCD14-ST in urine samples derived from healthy subjects and from patients having respiratory infection associated with bacterial infection, a cutoff value is set such that the sensitivity and/or specificity in detection of a disease can be optimized. The thus set cutoff value can be used as a reference value. It is, for example, 5000 pg/mL.

The method for determining the timing for ending administration of an antibiotic of the present invention can also be referred to as a method for selecting patients to end administration of an antibiotic from patients with respiratory infection receiving the antibiotic. By determining the timing for ending administration of an antibiotic, a patient becomes a target for ending administration of the antibiotic. Thus, the method for determining the timing for ending administration of an antibiotic has the same meanings as those of the method for selecting patients to end administration of an antibiotic. That is to say, the present invention provides a method for selecting patients to end administration of an antibiotic from patients with respiratory infection receiving the antibiotic by using measured values of sCD14-ST in urine samples derived from patients as indications. To the method for selecting patients to end administration of an antibiotic of the present invention, the aspect of the method for determining the timing for ending administration of an antibiotic can directly be applied.

4. Method for Treating Respiratory Infection Associated with Bacterial Infection The present invention provides a method for treating respiratory infection associated with bacterial infection. The treatment method of the present invention is characterized in that it comprises selecting patients with respiratory infection to receive an antibiotic by using the measured value of sCD14-ST in a urine sample derived from a subject as an indication, and this is a method for treating respiratory infection associated with bacterial infection by administering an antibiotic to the thus selected patients. Specifically, patients with respiratory infection to receive an antibiotic are selected by the method described in the aspect of 2. above, and the antibiotic is then administered to selected patients. Moreover, the timing for ending administration of an antibiotic is determined by the method described in the aspect of 3. above, so as to provide a more efficient treatment.

Moreover, the present invention provides a therapeutic agent (or a therapeutic pharmaceutical composition) for treating respiratory infection associated with bacterial infection, which is characterized in that it uses an antibiotic by a usage that is in accordance with the above-mentioned treatment method. The present therapeutic composition comprises an antibiotic as an active ingredient. The present therapeutic composition may comprise pharmaceutically acceptable any given additives and/or carriers, as well as an effective amount of antibiotic.

The types of antibiotics used in the inventions according to the aspects described in 2. to 5. above are not particularly limited. Antibiotics that can be applied to at least lower respiratory tract infection and/or pneumonia are preferable. Examples of such an antibiotic include penicillin antibiotics, penem antibiotics, carbapenem antibiotics, cephem antibiotics, monobactam antibiotics, fosfomycin antibiotics, glycopeptide antibiotics, aminoglycoside antibiotics, macrolide antibiotics, ketolide antibiotics, lincomycin antibiotics, tetracycline antibiotics, new quinolone antibiotics, sulfonamide antibiotics, oxazolidinone antibiotics, and streptogramin antibiotics. One or multiple antibiotics may be appropriately selected from these antibiotics and may be then used. For selection of antibiotics, known methods such as the method described in the Japanese Respiratory Society, "The Japanese Respiratory Society Guidelines for Management of Adult Community-Acquired Pneumonia" (*Asu no Rinsho*, Vol. 19, No. 1, pp. 41-61, 2007) may be applied.

Hereinafter, the present invention will be more specifically described in the following examples. However, these examples are not intended to limit the scope of the present invention.

EXAMPLES (Example 1) Production of sCD14-ST Measurement System (1-1) Preparation of Peroxidase-Labeled Antibody In order to produce a sandwich ELISA system, the F1106-13-3 antibody described in International Publication WO2004/044005 was labeled with peroxidase. First, the F1106-13-3 antibody was digested with Lysyl Endopeptidase (Wako Pure Chemical Industries, Ltd.) to produce F(ab')2. Specifically, the F1106-13-3 antibody was dialyzed against 50 mM Tris-HCl (pH 8.5), and the resulting antibody was then mixed with Lysyl Endopeptidase (wherein the molar ratio was 10:1). The obtained mixture was reacted at 37° C. for 1 hour. Thereafter, TLCK (Sigma) was added to the reaction product to a final concentration of 30 mM, so as to terminate the reaction. Subsequently, to remove Fc, the reaction solution was added to a Protein A column (Prosep-A; Millipore), and an unadsorbed product was then recovered. The thus recovered unadsorbed fraction was concentrated, and was then purified by gel filtration (Superdex 75; GE Healthcare), so that the contained F(ab')2 was separated from Fab. The obtained F(ab')2 was concentrated and was then dialyzed against a 10 mM carbonate buffer (pH 9.5).

Subsequently, in accordance with the method of Nakane et al. (J. Histochem. Cytochem., 22, 1084, 1974), 1 mg of peroxidase (Toyobo Co., Ltd.) was dissolved in distilled water, and 100 mM periodic acid dissolved in distilled water was then added thereto. The obtained mixture was reacted at 25° C. for 15 minutes. After completion of the reaction, 1.5% ethylene glycol was added to the reaction solution, and the obtained mixture was then reacted at 25° C. for 20 minutes. Thereafter, the reaction solution was dialyzed against a 1 mM acetate buffer (pH 4.4). On the following day, a 0.2 M carbonate buffer (pH 9.5) was added with respect to 1 mg of a F1106-13-3 F(ab')2 antibody, and 0.8 mg of activated peroxidase was then mixed with the above mixture. The thus obtained mixture was reacted at 25° C. for 2 hours. Then, 4 mg/mL sodium borohydride was added to the reaction solution, and the obtained mixture was further reacted at 4° C. for 2 hours. The reaction solution was dialyzed against PBS (pH 7.4) to obtain a peroxidase-labeled antibody. The amount of the liquid was measured, and an antibody concentration was then calculated based on the amount of the antibody used.

(1-2) Production of Sandwich EIA System

The S68-peptide polyclonal antibody described in International Publication WO2004/044005 was diluted with D-PBS (pH 7.4), resulting in a concentration of 5 μg/mL, and 50 μL of the antibody solution was then added to each well of an immunoplate (Maxisorp; NUNC). The antibody was reacted at 4° C. overnight, and it was then washed with ion exchange water five times. Thereafter, 200 μL of D-PBS that contained 0.1% StabilGuard (SurModics, Inc) and 0.1% Tween20 was added to each well to block it. Subsequently, D-PBS (pH 7.4) that contained 1% CD14 absorbed serum and 0.1% BSA was used as a diluent to prepare a dilution series of sCD14-ST protein standard products each having a concentration of 0, 0.015, 0.031, 0.063, 0.125, 0.25, or 0.5 ng/mL. As such a sCD14-ST protein standard product, rsCD14-ST described in International Publication WO2005/108429 was used. 50 μL each of the dilution series of the standard products was added to each well, and the obtained mixture was then reacted at 25° C. for 1 hour (a first reaction). After completion of the reaction, the reaction mixture was washed with a normal saline containing 0.05% Tween 20 five times. Thereafter, 50 μL of a F1106-13-3F(ab')2 antibody labeled with peroxidase that had been diluted to a concentration of 0.25 μg/mL with PBS (pH 7.4) containing 2% rat serum, 1% mouse serum and 0.1% Tween 20 was added to each well. The obtained mixture was reacted at 25° C. for 1 hour (a second reaction), and thereafter, the reaction mixture was washed five times in the same manner as described above. Thereafter, 50 μL of a tetramethylbenzidine solution (TMB, BioFix) was added to each well, and the obtained mixture was then reacted at room temperature for 20 minutes. After that, 50 μL of a 0.5 M sulfuric acid solution was added to the reaction mixture to terminate the reaction. The absorbance at 450/630 nm was measured using a plate spectrophotometer (Multiscan JX; Thermo Electron). It showed the standard curve produced in FIG. 1.

(Example 2) Measurement of sCD14-ST in Urine

Figure 2:
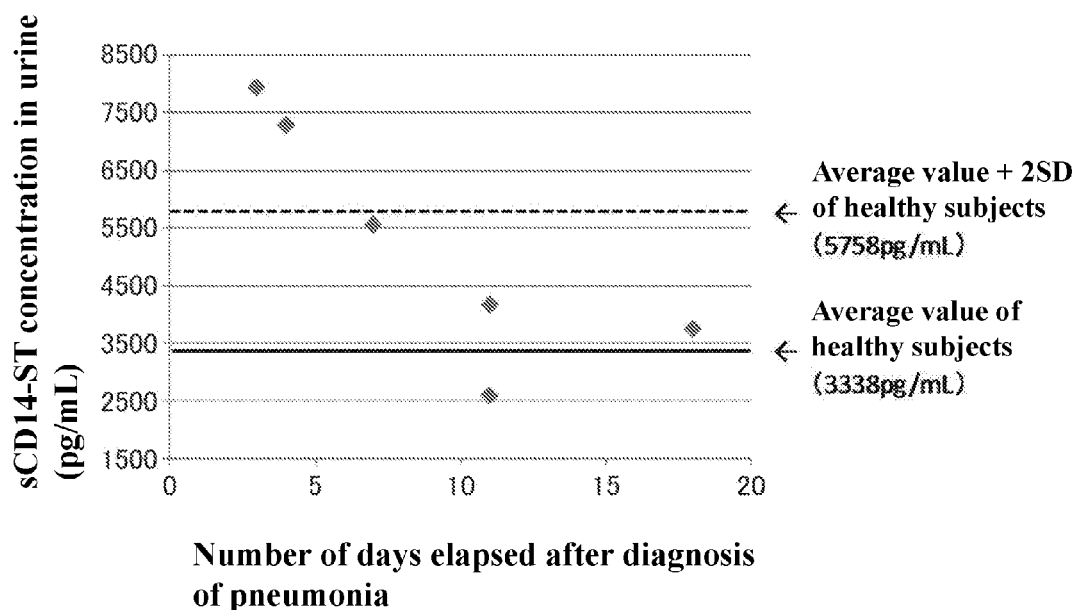
FIG. 2 is a view illustrating a distribution of the sCD14-ST concentrations in urine of pneumonia patients measured in Example 2. The horizontal axis indicates the number of days elapsed from the diagnosis of pneumonia to collection of the samples, and the longitudinal axis indicates the sCD14-ST concentration in urine. In the figure, the solid line indicates an average value (3338 pg/mL) of healthy subjects, and the dotted line indicates an average value+2SD (5758 pg/mL) of healthy subjects.

By using the sandwich EIA system prepared in Example 1, concentrations of sCD14-ST in urine samples (200-fold dilution) of 10 normal subjects (purchased from Bioreclamation, LLC) and of 6 patients with pneumonia associated with bacterial infection (community-acquired pneumonia) (purchased from Bioreclamation, LLC) were measured. As a result, as shown in Table 1, the average value of sCD14-ST concentration in urine samples of normal subjects was 3338 pg/mL, and SD was 1210 pg/mL. The average value of that of patients with pneumonia was 2591 to 7937 pg/mL. For reference, the concentration of sCD14-ST in a blood sample that had been collected on the same date as that of a urine sample derived from each of the pneumonia patients was measured. As a result, a fluctuation in sCD14-ST concentrations in urine correlated to a fluctuation in sCD15-ST concentrations in blood, and the concentration of sCD14-ST in urine was higher than that in blood by approximately 5 times. From these results, it was assumed that sCD14-ST in circulating blood would be relatively promptly concentrated and eliminated into urine. As shown in FIG. 2 in which the number of days from the day of diagnosis as pneumonia to the day of sampling was plotted on the abscissa and the concentration of sCD14-ST on the ordinate, the smaller number of days from diagnosis led to higher concentration and the larger number of days from diagnosis led to smaller concentration. In general, initiation of administering an antibiotic within 4 hours after diagnosis of pneumonia is recommended. Thus, it was demonstrated that patients with pneumonia associated with bacterial infection have higher sCD14-ST concentration in urine, and that symptomatic improvement by treatment and reduction in sCD14-ST concentration in urine are correlated. That is, it was demonstrated that, by using the sCD14-ST concentration in urine as an indication (for example, by using an average value of normal subjects+2SD as a cutoff value), respiratory infection associated with bacterial infection can be detected, and patients to receive an antibiotic can be selected. Also, it was shown that, when the sCD14-ST concentration in urine is lower than a reference value (for example, an average value of normal subjects+2SD, or for more strict conditions, an average value of normal subjects+SD), ending of administration of an antibiotic can be determined.

TABLE 1

| Sample No. | Classification | Number of days elapsed from diagnosis to sample collection | sCD14-ST concentration (pg/mL) |
|---|---|---|---|
| N1 | Normal | — | 2069 |
| N2 | Normal | — | 2143 |
| N3 | Normal | — | 2550 |
| N4 | Normal | — | 2994 |
| N5 | Normal | — | 5586 |
| N6 | Normal | — | 5252 |
| N7 | Normal | — | 2735 |
| N8 | Normal | — | 3771 |
| N9 | Normal | — | 2994 |
| N10 | Normal | — | 3290 |
| S1 | Pneumonia | 3 days | 7937 |
| S2 | Pneumonia | 4 days | 7291 |
| S3 | Pneumonia | 7 days | 5552 |
| S4 | Pneumonia | 11 days | 4170 |
| S5 | Pneumonia | 11 days | 2591 |
| S6 | Pneumonia | 18 days | 3749 |

(Example 3) Selection of Patients with Respiratory Infection to Receive an Antibiotic by Using the sCD14-ST Concentration as an Indication Patients showing at least breathing difficulty or cough as a clinical finding and suspected to have respiratory infection are assigned to a control group to receive usual treatment with an antibiotic, and a sCD14-ST group to receive treatment with the antibiotic by using the sCD14-ST concentration as an indication. The control group patients receive the antibiotic at a physician's discretion as usual. The sCD14-ST group patients receive the antibiotic depending on a measured value of sCD14-ST in a urine sample; when the measured value of sCD14-ST is higher than a normal value, administration of the antibiotic is recommended, and when the measured value of sCD14-ST is equal to the normal value or lower than the normal value, administration of the antibiotic is not recommended.

Symptomatic improvement in both groups of patients is evaluated at 2, 4, 6, or 8 weeks after initiation of the study. Administration of the antibiotic until 2 or 4 weeks after initiation of the study is also evaluated. As additional information, where appropriate, pneumonia, bronchitis, acute exacerbation of chronic obstructive pulmonary disease, bronchial asthma, and the like of respiratory tract infections in both groups of patients are checked based on X-ray shadow, blood testing, respiratory function testing, and the like.

Symptomatic improvement is evaluated as improvement of clinical findings. As additional end points, self-health-evaluation by patients (VAS, QOL questionnaire, and the like), and measured values of sCD14-ST may be added.

As a result, there is no difference in symptomatic improvement between both groups. However, administration of the antibiotic is significantly reduced in the sCD14-ST group. Furthermore, it is demonstrated that, in the sCD14-ST group, the sub-group of patients with a disease often associated with bacterial infection (for example, pneumonia) have a higher percentage of receiving the antibiotic, and the other sub-group of patients with a disease rarely associated with bacterial infection (for example, bronchial asthma) have a lower percentage of receiving the antibiotic.

Therefore, by using the sCD14-ST concentration as an indication, patients with respiratory infection to receive an antibiotic can be appropriately selected, and usage of an antibiotic (number of patients to receive the antibiotic, amount of the antibiotic to receive, duration to receive, or number of prescriptions) can be reduced without being destructive to the safety and the efficacy of the antibiotic therapy.

(Example 4) Optimization of Duration to Receive an Antibiotic in Patients with Pneumonia by Using the sCD14-ST Concentration as an Indication Patients whose condition is diagnosed as pneumonia based on clinical findings and to receive an antibiotic are assigned to a control group to receive usual treatment with the antibiotic, and a sCD14-ST group to receive treatment with the antibiotic by using the sCD14-ST concentration as an indication. The control group patients stop receiving the antibiotic at a physician's discretion as usual. The sCD14-ST group patients receive the antibiotic depending on a measured value of sCD14-ST in a urine sample; when the measured value of sCD14-ST is equal to the normal value or lower than the normal value, ending administration of the antibiotic is recommended. The measured value of sCD14-ST is preferably obtained over time (for example, every day after initiation of receiving the antibiotic).

Symptomatic improvement in both groups of patients is evaluated at 2, 4, 6, or 8 weeks after initiation of administrating the antibiotic. A period elapsed until administration of the antibiotic has been terminated is also evaluated. As additional information, severity of pneumonia in both groups of patients is determined.

Symptomatic improvement is evaluated as improvement of clinical findings. In particular, curing of pneumonia is preferably checked. As additional end points, self-health-evaluation by patients (VAS, QOL questionnaire, and the like), and measured values of sCD14-ST may be added.

As a result, there is no difference in symptomatic improvement between both groups. However, administrating duration of the antibiotic is significantly reduced in the sCD14-ST group.

Therefore, by using the sCD14-ST concentration as an indication, timing for ending administration of the antibiotic can be appropriately determined, and duration of administering the antibiotic can be reduced without being destructive to the safety and the efficacy of the antibiotic therapy.

(Example 5) Measurement of sCD14-ST in Urine

Figure 3:
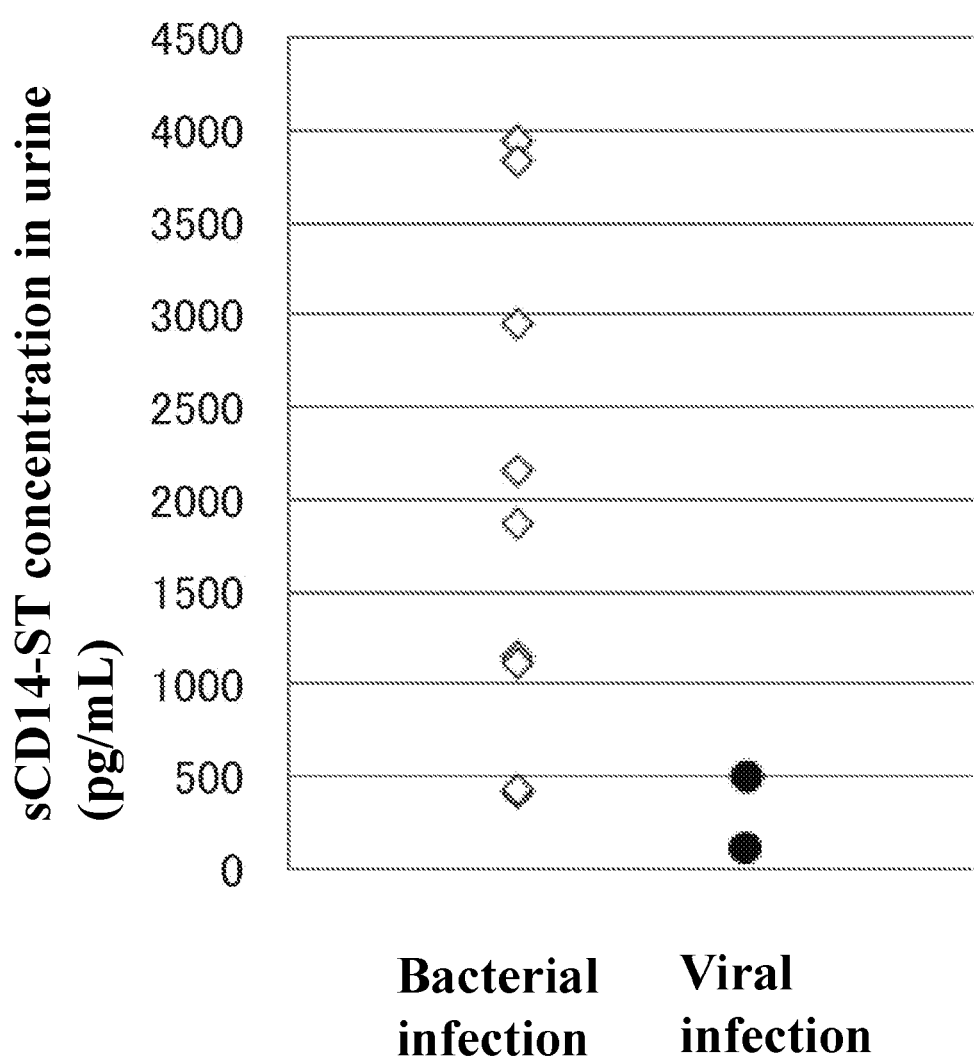
FIG. 3 is a view illustrating a distribution of the sCD14-ST concentrations in urine of pneumonia patients with bacterial infection and pneumonia patients with viral infection, which were measured in Example 5. The longitudinal axis indicates the sCD14-ST concentration in urine.

Measurement conditions applied to the sandwich EIA system prepared in Example 1 were revised, and the first reaction conditions described in Example 1 were changed to 25° C. for 1 hour, and the second reaction conditions to 25° C. for 2 hours. By using this system, concentrations of sCD14-ST in urine samples (5-fold dilution) of 9 patients with pneumonia associated with bacterial infection and of 2 patients with viral pneumonia (purchased from Bioreclamation, Inc.) were measured. As a result, sCD14-ST concentrations in urine of patients with pneumonia associated with bacterial infection were 419 to 3859 pg/mL (median, 1885 pg/mL), and those of patients with viral pneumonia were 115 to 517 pg/mL (median, 316 pg/mL). Accordingly, sCD14-ST concentrations in urine of patients with viral pneumonia were lower than the average value of normal subjects, and were clearly lower than those of patients with pneumonia associated with bacterial infection needing administration of the antibiotic (FIG. 3). Therefore, it was indicated that measuring sCD14-ST in a urine sample can distinguish respiratory infection associated with bacterial infection from viral respiratory infection.

(Example 6) Elimination of sCD14-ST from Blood into Urine

Rate of sCD14-ST elimination from blood into urine was determined. To 3 dogs (male beagle dogs, 7 or 8 months old, purchased from Kitayama Labes Co., Ltd.), recombinant sCD14-ST (rsCD14-ST described in WO 2005/108429) at a dose of 10 μg/kg was administered intravenously, and the blood and urine were collected over time until 24 hours after administration. By using the sandwich EIA system described in Example 1, the concentration of sCD14-ST in blood and the amount of sCD14-ST in urine were measured. The amount of sCD14-ST in urine was calculated according to the formula: the concentration of sCD-14ST in urine (pg/mL)×the amount of urine (mL).

The blood was collected before administration, 5 minutes, 10 minutes, 30 minutes, 60 minutes, 90 minutes, 120 minutes, 4 hours, and 24 hours after administration, and centrifuged plasma was used as the measuring sample. The urine was collected by urethral catheterization under unanesthetized conditions. As much as amount of urine remaining in the bladder was collected before administration, and 15 minutes, 30 minutes, 60 minutes, 90 minutes, 120 minutes, 150 minutes, 6 hours and 24 hours after administration. Moreover, after completion of the urine collection, 100 mL of a normal saline was orally administered to each dog before administration of the sCD14-ST.

Figure 4:
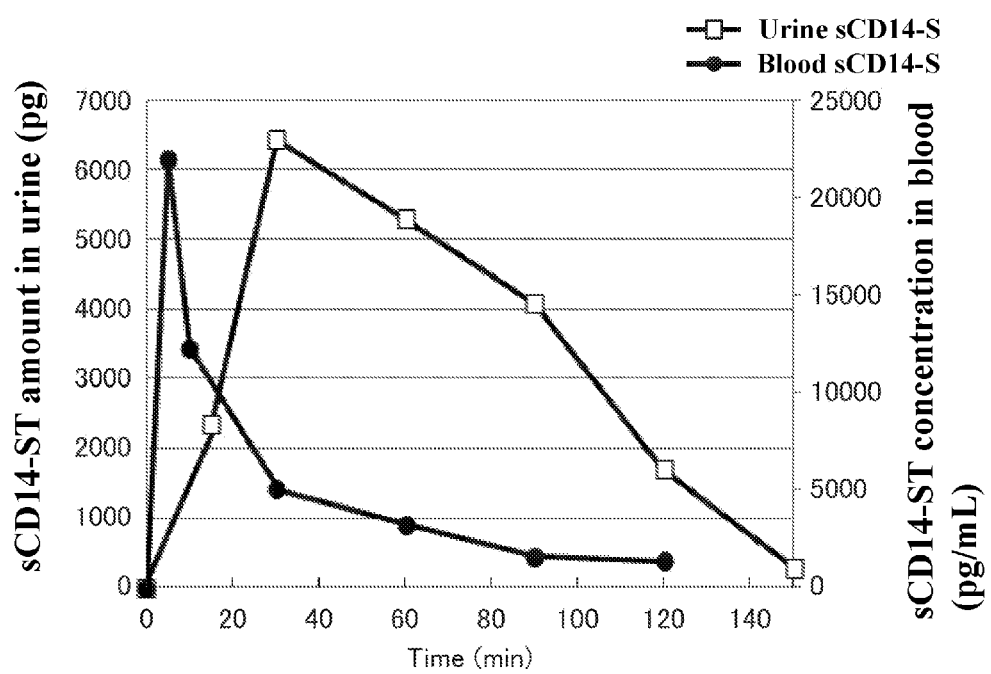
FIG. 4 is a view illustrating a transition in the sCD14-ST concentrations in blood and a transition in the sCD14-ST amounts in urine in the case of intravenous administration of sCD14-ST, which were measured in Example 6. The horizontal axis indicates the time elapsed after completion of the administration. The left longitudinal axis indicates the sCD14-ST amount in urine, and the right longitudinal axis indicates the sCD14-ST concentration in blood.

FIG. 4 illustrates the transition in sCD14-ST concentrations in blood and the transition in sCD14-ST amounts in urine. The half-life of sCD14-ST in blood was 25 minutes within 1 hour after administration, and then was 58 minutes, and thus, sCD14-ST in blood showed a biphasic kinetics. Concentration of sCD14-ST in blood 120 minutes after administration reduced to approximately 6% of the blood concentration 5 minutes after administration, and sCD14-ST was completely eliminated from blood 24 hours after administration. The amount of sCD14-ST in urine reached a peak 30 minutes after administration, and then, 150 minutes after administration, the amount of sCD14-ST in urine reduced to approximately 4% of that of the peak time. Twenty-four hours after administration, sCD14-ST completely disappeared from urine. From these results, it became clear that the blood sCD14-ST begins to be eliminated into urine within 1 hour after administration, and that most of sCD14-ST is then eliminated even from urine within 3 hours after administration. The appearance and elimination of sCD14-ST in urine take place very promptly, and are considered to sensitively reflect the movement of sCD14-ST generated in a body by bacterial infection. That is to say, it was demonstrated that when bacterial infection in respiratory organs is decreased or eliminated, the sCD14-ST concentration in urine is also reduced rapidly, and it can be appropriately used for determination of ending administration of an antibiotic, and the like.

The invention claimed is:

1. A method for detecting a respiratory infection associated with a bacterial infection in a subject in need thereof, comprising:
   (1) measuring soluble CD14 antigen subtype ("sCD14-ST") in a urine sample derived from the subject;
   (2) comparing a measured value of sCD14-ST with a cutoff value;
   (3) discriminating between bacterial and viral infections based on the measured value of sCD14-ST;
   wherein an increase in said measured value of sCD14-ST compared to said cutoff value is indicative of the respiratory infection associated with the bacterial infection and a decrease in said measured value of sCD14-ST compared to said cutoff value is indicative of the respiratory infection associated with the viral infection;
   wherein said cutoff value is in a range from 3,338 pg/mL to 5,758 pg/mL;
   wherein the sCD14-ST is measured by a sandwich immunoassay system comprising:
      (a) an antibody binding to a peptide comprising an amino acid sequence of SEQ ID No: 2, and
      (b) an antibody binding to a peptide comprising an amino acid sequence from positions 17 to 26 of SEQ ID NO: 3.

2. A method for detecting a respiratory infection associated with a bacterial infection in a subject in need thereof, which comprises the following steps of:
   (1) measuring sCD14-ST in a urine sample derived from the subject; and
   (2) determining whether or not the subject is affected with the respiratory infection associated with the bacterial infection by comparing a measured value of sCD14-ST in the sample with a cutoff value;
   wherein an increase in the measured value of sCD14-ST compared to the cutoff value is indicative of the respiratory infection associated with the bacterial infection;
   wherein said cutoff value is in a range from 3,338 pg/mL to 5,758 pg/mL;
   wherein the sCD14-ST is measured by a sandwich immunoassay system comprising:
      (a) an antibody binding to a peptide comprising an amino acid sequence of SEQ ID No: 2, and
      (b) an antibody binding to a peptide comprising an amino acid sequence from positions 17 to 26 of SEQ ID NO: 3.

3. The method according to claim 1, wherein the respiratory infection associated with the bacterial infection is a lower respiratory tract infection or pneumonia.

4. The method according to claim 2, wherein the respiratory infection associated with the bacterial infection is a lower respiratory tract infection or pneumonia.

5. A method for selecting a patient with a respiratory infection to receive an antibiotic, comprising:
   (1) measuring sCD14-ST in a urine sample derived from the patient; and
   (2) determining whether or not the patient is affected with the respiratory infection associated with a bacterial infection by using a measured value of sCD14-ST in the sample as an indication, wherein an increased measured value of sCD14-ST compared to a cutoff value is indicative of the respiratory infection associated with the bacterial infection;
   (3) selecting said patient with said increased measured value of sCD14-ST to receive an antibiotic;
   wherein said cutoff value is in a range from 3,338 pg/mL to 5,758 pg/mL;
   wherein the sCD14-ST is measured by a sandwich immunoassay system comprising:
      (a) an antibody binding to a peptide comprising an amino acid sequence of SEQ ID No: 2, and
      (b) an antibody binding to a peptide comprising an amino acid sequence from positions 17 to 26 of SEQ ID NO: 3.

6. The method according to claim 5, wherein the respiratory infection is a lower respiratory tract infection or pneumonia.

7. A method for determining a timing for ending administration of an antibiotic to a patient with a respiratory infection receiving the antibiotic, wherein a measured value of sCD14-ST in a urine sample derived from the patient is used as an indication,
   wherein a decrease in the measured value of sCD14-ST compared to a cutoff value is indicative of the timing for ending administration of the antibiotic to the patient;
   wherein said cutoff value is in a range from 3,338 pg/mL to 5,758 pg/mL;
   wherein the sCD14-ST is measured by a sandwich immunoassay system comprising:
      (a) an antibody binding to a peptide comprising an amino acid sequence of SEQ ID No: 2, and
      (b) an antibody binding to a peptide comprising an amino acid sequence from positions 17 to 26 of SEQ ID NO: 3.

8. A method for determining a timing for ending administration of an antibiotic to a patient with a respiratory infection receiving the antibiotic, which comprises the following steps of:
   (1) measuring sCD14-ST in a urine sample derived from the patient;
   (2) comparing a measured value of sCD14-ST in the sample with a cutoff value; and
   (3) when the measured value of the sample is lower than the cutoff value, determining to end administration of the antibiotic;
   wherein said cutoff value is in a range from 3,338 pg/mL to 5,758 pg/mL;
   wherein the sCD14-ST is measured by a sandwich immunoassay system comprising:
      (a) an antibody binding to a peptide comprising an amino acid sequence of SEQ ID No: 2, and
      (b) an antibody binding to a peptide comprising an amino acid sequence from positions 17 to 26 of SEQ ID NO: 3.

9. A method for selecting a patient to end administration of an antibiotic from the patient with a respiratory infection receiving the antibiotic comprising using a measured value of sCD14-ST in a urine sample derived from the patient as an indication;
   wherein a decrease in the measured value of sCD14-ST compared to a cutoff value is indicative of the patient to end administration of the antibiotic;
   wherein said cutoff value is in a range from 3,338 pg/mL to 5,758 pg/mL;
   wherein the sCD14-ST is measured by a sandwich immunoassay system comprising:
      (a) an antibody binding to a peptide comprising an amino acid sequence of SEQ ID No: 2, and
      (b) an antibody binding to a peptide comprising an amino acid sequence from positions 17 to 26 of SEQ ID NO: 3.

10. A method for selecting a patient for whom to end administration of an antibiotic, wherein the patient has a respiratory infection and is receiving the antibiotic, which comprises the following steps of:
(1) measuring sCD14-ST in a urine sample derived from a patient;
(2) comparing a measured value of sCD14-ST in the sample with a cutoff value; and
(3) when the measured value of the sample is lower than the cutoff value, determining to end administration of the antibiotic;
wherein said cutoff value is in a range from 3,338 pg/mL to 5,758 pg/mL;
wherein the sCD14-ST is measured by a sandwich immunoassay system comprising:
(a) an antibody binding to a peptide comprising an amino acid sequence of SEQ ID No: 2, and
(b) an antibody binding to a peptide comprising an amino acid sequence from positions 17 to 26 of SEQ ID NO: 3.

11. The method according claim 6, wherein the respiratory infection is a lower respiratory tract infection or pneumonia.

12. The method according to claim 7, wherein the respiratory infection is a lower respiratory tract infection or pneumonia.

13. The method according to claim 8, wherein the respiratory infection is a lower respiratory tract infection or pneumonia.

14. The method according to claim 9, wherein the respiratory infection is a lower respiratory tract infection or pneumonia.

15. A method for treating a respiratory infection associated with a bacterial infection, which comprises the following steps of:
(1) measuring sCD14-ST in a urine sample derived from a patient;
(2) selecting the patient to receive an antibiotic by using a measured value of sCD14-ST in the sample as an indication; and
(3) administering the antibiotic to the selected patient;
wherein an increase in the measured value of sCD14-ST compared to a cutoff value is indicative of the patient to receive the antibiotic;
wherein said cutoff value is in a range from 3,338 pg/mL to 5,758 pg/mL;
wherein the sCD14-ST is measured by a sandwich immunoassay system comprising:
(a) an antibody binding to a peptide comprising an amino acid sequence of SEQ ID No: 2, and
(b) an antibody binding to a peptide comprising an amino acid sequence from positions 17 to 26 of SEQ ID NO: 3.

16. The method according to claim 15, wherein the step of selecting the patient to receive the antibiotic by using the measured value of sCD14-ST in the sample as the indication comprises the following steps of:
(1) comparing the measured value of sCD14-ST in the sample with a cutoff value; and
(2) selecting the patient to receive the antibiotic whose measured value in the sample is higher than the cutoff value;
wherein said cutoff value is in a range from 3,338 pg/mL to 5,758 pg/mL;
wherein the sCD14-ST is measured by a sandwich immunoassay system comprising:
(a) an antibody binding to a peptide comprising an amino acid sequence of SEQ ID No: 2, and
(b) an antibody binding to a peptide comprising an amino acid sequence from positions 17 to 26 of SEQ ID NO: 3.

17. The method according to claim 15, which further comprises the following steps of:
(1) measuring sCD14-ST in the urine sample derived from the patient receiving the antibiotic until determining to end administration of the antibiotic;
(2) comparing the measured value of sCD14-ST in the sample with a cutoff value; and
(3) when the measured value of the sample is lower than the cutoff value, determining to end administration of the antibiotic;
wherein said cutoff value is in a range from 3,338 pg/mL to 5,758 pg/mL;
wherein the sCD14-ST is measured by a sandwich immunoassay system comprising:
(a) an antibody binding to a peptide comprising an amino acid sequence of SEQ ID No: 2, and
(b) an antibody binding to a peptide comprising an amino acid sequence from positions 17 to 26 of SEQ ID NO: 3.

18. The method according to claim 15, wherein the respiratory infection associated with the bacterial infection is a lower respiratory tract infection or pneumonia.

19. A method for detecting a respiratory infection associated with a bacterial infection in a subject in need thereof, comprising measuring soluble CD14 antigen subtype ("sCD14-ST") in a urine sample derived from the subject;
wherein an increase in a measured value of sCD14-ST is indicative of the respiratory infection associated with the bacterial infection;
wherein the sCD14-ST level above a cutoff value indicates a need for the subject to receive an antibiotic,
wherein the cutoff value is in a range from 3,338 pg/mL to 5,758 pg/mL;
wherein the sCD14-ST is measured by a sandwich immunoassay system comprising:
(a) an antibody binding to a peptide comprising an amino acid sequence of SEQ ID No: 2, and
(b) an antibody binding to a peptide comprising an amino acid sequence from positions 17 to 26 of SEQ ID NO: 3.

20. A method of treating a respiratory infection associated with a bacterial infection comprising administering an antibiotic to a patient having an sCD14-ST level in urine above a cutoff value;
wherein the cutoff value is in a range from 3,338 pg/mL to 5,758 pg/mL;
wherein the sCD14-ST is measured by a sandwich immunoassay system comprising:
(a) an antibody binding to a peptide comprising an amino acid sequence of SEQ ID No: 2, and
(b) an antibody binding to a peptide comprising an amino acid sequence from positions 17 to 26 of SEQ ID NO: 3.

* * * * *

SEQUENCE LISTING

```
<160> NUMBER OF SEQ ID NOS: 3

<210> SEQ ID NO 1
<211> LENGTH: 11
<212> TYPE: PRT
<213> ORGANISM: Homo sapiens

<400> SEQUENCE: 1

Thr Thr Pro Glu Pro Cys Glu Leu Asp Asp Glu
1               5                   10

<210> SEQ ID NO 2
<211> LENGTH: 16
<212> TYPE: PRT
<213> ORGANISM: Homo sapiens

<400> SEQUENCE: 2

Arg Val Asp Ala Asp Ala Asp Pro Arg Gln Tyr Ala Asp Thr Val Lys
1               5                   10                  15
```

```
<210> SEQ ID NO 3
<211> LENGTH: 356
<212> TYPE: PRT
<213> ORGANISM: Homo sapiens

<400> SEQUENCE: 3

Thr Thr Pro Glu Pro Cys Glu Leu Asp Asp Glu Asp Phe Arg Cys Val
1               5                   10                  15

Cys Asn Phe Ser Glu Pro Gln Pro Asp Trp Ser Glu Ala Phe Gln Cys
                20                  25                  30

Val Ser Ala Val Glu Val Glu Ile His Ala Gly Gly Leu Asn Leu Glu
            35                  40                  45

Pro Phe Leu Lys Arg Val Asp Ala Asp Ala Asp Pro Arg Gln Tyr Ala
    50                  55                  60

Asp Thr Val Lys Ala Leu Arg Val Arg Arg Leu Thr Val Gly Ala Ala
65                  70                  75                  80

Gln Val Pro Ala Gln Leu Leu Val Gly Ala Leu Arg Val Leu Ala Tyr
                85                  90                  95

Ser Arg Leu Lys Glu Leu Thr Leu Glu Asp Leu Lys Ile Thr Gly Thr
            100                 105                 110

Met Pro Pro Leu Pro Leu Glu Ala Thr Gly Leu Ala Leu Ser Ser Leu
        115                 120                 125

Arg Leu Arg Asn Val Ser Trp Ala Thr Gly Arg Ser Trp Leu Ala Glu
    130                 135                 140

Leu Gln Gln Trp Leu Lys Pro Gly Leu Lys Val Leu Ser Ile Ala Gln
145                 150                 155                 160

Ala His Ser Pro Ala Phe Ser Cys Glu Gln Val Arg Ala Phe Pro Ala
                165                 170                 175

Leu Thr Ser Leu Asp Leu Ser Asp Asn Pro Gly Leu Gly Glu Arg Gly
            180                 185                 190

Leu Met Ala Ala Leu Cys Pro His Lys Phe Pro Ala Ile Gln Asn Leu
        195                 200                 205

Ala Leu Arg Asn Thr Gly Ile Glu Thr Pro Thr Gly Val Cys Ala Ala
    210                 215                 220

Leu Ala Ala Ala Gly Val Gln Pro His Ser Leu Asp Leu Ser His Asn
225                 230                 235                 240

Ser Leu Arg Ala Thr Val Asn Pro Ser Ala Pro Arg Cys Met Trp Ser
                245                 250                 255

Ser Ala Leu Asn Ser Leu Asn Leu Ser Phe Ala Gly Leu Glu Gln Val
            260                 265                 270

Pro Lys Gly Leu Pro Ala Lys Leu Arg Val Leu Asp Leu Ser Cys Asn
        275                 280                 285

Arg Leu Asn Arg Ala Pro Gln Pro Asp Glu Leu Pro Glu Val Asp Asn
    290                 295                 300

Leu Thr Leu Asp Gly Asn Pro Phe Leu Val Pro Gly Thr Ala Leu Pro
305                 310                 315                 320

His Glu Gly Ser Met Asn Ser Gly Val Val Pro Ala Cys Ala Arg Ser
                325                 330                 335

Thr Leu Ser Val Gly Val Ser Gly Thr Leu Val Leu Leu Gln Gly Ala
            340                 345                 350

Arg Gly Phe Ala
    355
```